United States Patent
Altrogge et al.

(10) Patent No.: US 9,649,166 B2
(45) Date of Patent: May 16, 2017

(54) ABLATED OBJECT REGION DETERMINING APPARATUSES AND METHODS

(71) Applicant: Fraunhofer Gesellschaft zur Förderung der angewandten Forschung e.V., München (DE)

(72) Inventors: Inga Altrogge, Bremen (DE); Tim Kroeger, Bremen (DE); Heinz-Otto Peitgen, Bremen (DE); Tobias Preusser, Bremen (DE)

(73) Assignee: Fraunhofer Gesellschaft zur Förderung der angewandten Forschung e.V., München (DE)

( * ) Notice: Subject to any disclaimer, the term of this patent is extended or adjusted under 35 U.S.C. 154(b) by 384 days.

(21) Appl. No.: 14/067,372

(22) Filed: Oct. 30, 2013

(65) Prior Publication Data

US 2014/0128884 A1  May 8, 2014

Related U.S. Application Data

(62) Division of application No. 12/702,639, filed on Feb. 9, 2010, now Pat. No. 8,600,719.

(51) Int. Cl.
| | |
|---|---|
| *G01N 33/48* | (2006.01) |
| *A61B 19/00* | (2006.01) |
| *G06F 19/00* | (2011.01) |
| *G06F 19/12* | (2011.01) |
| *G06G 7/58* | (2006.01) |
| *A61B 18/02* | (2006.01) |
| *A61B 18/14* | (2006.01) |
| *A61B 34/10* | (2016.01) |
| *A61B 34/20* | (2016.01) |
| *A61B 90/00* | (2016.01) |

(52) U.S. Cl.
CPC .............. *A61B 19/50* (2013.01); *A61B 34/10* (2016.02); *G06F 19/12* (2013.01); *G06F 19/30* (2013.01); *A61B 18/02* (2013.01); *A61B 18/1477* (2013.01); *A61B 2018/1425* (2013.01); *A61B 2034/104* (2016.02); *A61B 2034/105* (2016.02); *A61B 2034/2051* (2016.02); *A61B 2034/2055* (2016.02); *A61B 2090/365* (2016.02); *A61B 2090/3762* (2016.02)

(58) Field of Classification Search
None
See application file for complete search history.

(56) References Cited

U.S. PATENT DOCUMENTS

| | | |
|---|---|---|
| 6,553,356 B1 | 4/2003 | Good et al. |
| 7,490,988 B1 | 2/2009 | Yan |
| 7,865,002 B2 | 1/2011 | Basilico et al. |
| 2007/0167943 A1* | 7/2007 | Janssen .............. A61B 18/1477 606/41 |
| 2007/0280525 A1 | 12/2007 | Basilico et al. |
| 2008/0292164 A1 | 11/2008 | Azar et al. |
| 2012/0114213 A1 | 5/2012 | Buelow et al. |

FOREIGN PATENT DOCUMENTS

| | | |
|---|---|---|
| WO | 2008151113 | 12/2008 |
| WO | 2011007312 | 1/2011 |

OTHER PUBLICATIONS

Altrogge, I. et al., "Multi-Scale Optimization of the Probe Placement for Radio-Frequency Ablation," Acad. Rad. 14(11), 2007, 12 pages.
Chang, Isaac A. and Nguyen, Uyen D., "Thermal modeling of lesion growth with radiofrequency ablation devices," BioMedical Engineering OnLine, 3:27, published Aug. 6, 2004, 19 pages.
Kroeger, Tim et al., "Numerical Simulation of Radio Frequency Ablation with State Dependent Material Parameters in Three Space Dimensions," Lecture Notes on Computer Science 4191, published 2006, pp. 380-388.
Wood, Bradford J. et al., "Technologies for Guidance of Radiofrequency Ablation in the Multimodality Interventional Suite of the Future," Journal of Vascular Interventional Radiology, Jan. 2007, 18:9-24.
European Patent Office; International Search Report and Written Opinion for PCT/EP2011/053134; Completed May 31, 2011; Mailed Jun. 14, 2011; 14 pages.
Sun et al., "Ipsilateral-mammogram computer-aided detection of breast cancer," Computerized Medical Imaging and Graphics 28 (2004) 151-158.
Yuan-Hsiang Chang, Phd., et al.; Computerized Localization of Breast Lesions From Two Views An Experimental Comparison of Two Methods; Investigative Radiology, Sep. 1999; vol. 34; No. 9; pp. 585-588; 4 pages.

(Continued)

*Primary Examiner* — Eric S Dejong
(74) *Attorney, Agent, or Firm* — Ellen M. Bierman; Lowe Graham Jones PLLC

(57) ABSTRACT

Ablated object region determining apparatuses and methods for determining an ablated object region for ablating an object of interest are provided. A user can set an orientation and position of an ablation element with respect to a geometrical representation of the object of interest, at least one energy influencing element and a spatial relationship between the object of interest and the at least one energy influencing element. A model ablation region retrieving unit retrieves a model ablation region depending on the respective set orientation and position of the ablation element from a model ablation region storing unit. An ablated object region determining unit determines at least one of a) an ablated object region of the object of interest being located within the retrieved model ablation region and b) a non-ablated object region of the object of interest being located outside the retrieved model ablation region.

4 Claims, 9 Drawing Sheets

(56) References Cited

OTHER PUBLICATIONS

Xuejun Sun et al.; Ipsilateral Multi-view CAD System for Mass Detection in Digital Mammography; Mathematical Methods in Biomedical Image Analysis, Dec. 9, 2001; pp. 19-26; 8 pages.

* cited by examiner

ABLATED OBJECT REGION DETERMINING APPARATUSES AND METHODS

CROSS-REFERENCE TO RELATED APPLICATIONS

This application is a division of U.S. patent application Ser. No. 12/702,639 entitled "ABLATED OBJECT REGION DETERMINING APPARATUSES AND METHODS," filed on Feb. 9, 2010 now U.S. Pat. No. 8,600,719, which is incorporated herein by reference in its entirety.

TECHNICAL FIELD

The present disclosure relates to an ablated object region determining apparatus, an ablated object region determining method and an ablated object region determining computer program for planning an ablation procedure for ablating an object of interest. The present disclosure relates further to a model ablation region determining apparatus, a model ablation region determining method and a model ablation region determining computer program for determining model ablation regions. Moreover, the present disclosure relates to an arranging apparatus, an arranging method and an arranging computer program for arranging an ablation element within an object.

BACKGROUND

The article "Technologies for Guidance of Radiofrequency Ablation in the Multimodality Interventional Suite of the Future", Bradford J. Wood et al., Journal of Vascular Interventional Radiology, 2007 Jan., 18: pages 9 to 24 discloses methods for ablation planning for ablating an object of interest like a tumor or metastasis. The methods include calculating a temperature distribution under consideration of an arrangement of an ablation element with respect to the object of interest and with respect to blood vessels having a cooling effect and determining the parts of the object of interest having a temperature being large enough for ablating these parts. If there are parts of the object having temperatures being too small for being ablated, the orientation and/or position of the ablation element can be modified and the calculation of the temperature distribution and the determination of the parts of the object of interest with temperatures being large enough for being ablated can be repeated. This modification, calculation and determination procedure is repeated until an orientation and position of the ablation element has been found which allow ablating the object of interest completely.

For calculating the temperature distribution complicated non-linear differential equations have to be solved, where the nonlinearity arises from the fact that for example, material parameters like the thermal conductivity of tissue change with temperature. This calculation of the temperature distribution requires high computational costs leading to a long period of time needed for ablation planning.

SUMMARY

This disclosure describes an ablated object region determining apparatus, an ablated object region determining method and an ablated object region determining computer program for determining an ablated object region for ablating an object of interest, wherein the determination of an ablated object region can be accurately achieved within a shorter period of time, in particular, within a few seconds, interactively. The disclosure relates further to a corresponding model ablation region determining apparatus, model ablation region determining method and model ablation region determining computer program for determining model ablation regions, and to a corresponding arranging apparatus, arranging method and arranging computer program for arranging an ablation element within or in the vicinity of an object of interest.

In one aspect an ablated object region determining apparatus for determining an ablated object region for ablating an object of interest is presented, wherein the ablated object region determining apparatus comprises:

a geometrical representation providing unit for providing a geometrical representation of the object of interest, of at least one energy influencing element and of a spatial relationship between the object of interest and the at least one energy influencing element, an ablation element setting unit for allowing a user to set an orientation and position of an ablation element with respect to the provided geometrical representation, a model ablation region storing unit, in which model ablation regions are stored depending on a spatial relationship between a model ablation element and at least one model energy influencing element, wherein a model ablation region defines a region, which will be ablated given a respective spatial relationship between the model ablation element and the at least one model energy influencing element, a model ablation region retrieving unit for retrieving a model ablation region, which corresponds to the spatial relationship between the ablation element in the set orientation and in the set position and the at least one energy influencing element represented by the provided geometrical representation, from the model ablation region storing unit, an ablated object region determining unit for determining at least one of a) an ablated object region of the object of interest being located within the retrieved model ablation region and b) a non-ablated object region of the object of interest being located outside the retrieved model ablation region.

Since the model ablation regions are predetermined and since the respective model ablation region has just to be retrieved from the model ablation region storing unit by the model ablation region retrieving unit, an accurately determined ablated object region can quickly be provided for ablation planning. The determination of the model ablation regions is decoupled from the determination of at least one of an ablated object region and of a non-ablated object region of the object of interest. The model ablation regions can therefore be determined in advance very accurately, and even if this accurate determination of the model ablation regions takes a relatively long time, this does not affect the time needed for determining at least one of an ablated object region and a non-ablated object region of the object of interest. Thus, the ablated object region determining apparatus allows determining an ablated object region accurately and very fast, in particular, within a few seconds, interactively.

In some embodiments, the ablated object region determining unit further comprises a display unit for visualizing the ablated object region of the object and the non-ablated object region of the object differently, if the ablated object region determining unit has determined an ablated object region of the object of interest and a non-ablated object region of the object of interest.

In some embodiments, the geometrical representation providing unit comprises an image data set providing unit for providing a segmented image data set representing the object of interest, at least one energy influencing element and a spatial relationship between the object of interest and the at least one energy influencing element.

In some embodiments, the image data set is a medical image data set showing the entire body or a part of a body of a person or of an animal. For example, the image data set is an image data set showing an organ like the lung or the liver.

In some embodiments, the image data set is generated by an imaging modality like a computed tomography imaging system, a magnetic resonance imaging system, a nuclear medicine imaging system like a positron emission tomography system or a single photon emission computed tomography imaging system, or an ultrasound imaging system.

In some embodiments, the object of interest is a lesion, a metastasis or a primary tumor and the at least one energy influencing element is a blood vessel. The object of interest and the at least one energy influencing element can be segmented by using known techniques like thresholding.

The image data set providing unit can comprise at least one of the above mentioned imaging systems for generating the image data set and a segmentation unit for segmenting at least the object of interest and the at least one energy influencing element within the image data set. The image data set providing unit can also be a storing unit, in which the segmented image data set is stored. Moreover, the image data set providing unit can be a receiving unit for receiving the segmented image data set and for providing the received segmented image data set to the ablation element setting unit. The receiving unit can be adapted for receiving the segmented image data set via a wired or wireless data link.

A geometrical description of the ablation element and/or the at least one energy influencing element can be provided as one or several of the following:
  one or several cylinders having circular or polygonal cross-section, parameterized by the radius, height, position, and orientation of the one or several cylinders;
  a number of polyhedra that make up a closed surface, where the polyhedra are for example parameterized by the coordinates of their vertices;
  an implicit function representation, that is, a real-valued function on a three-dimensional set that takes values of a certain sign inside the ablation element (or inside the at least one energy influencing element, respectively) and values of the opposite sign outside the ablation element (or inside the at least one energy influencing element, respectively).

In addition to providing the geometrical representation of the object of interest and the at least on energy influencing element, the geometrical representation providing unit can be adapted to additionally provide the geometry and the spatial relation of structures in the body of a person or an animal, which are in the vicinity of the object of interest. For example, the geometrical representation providing unit describes the geometry of and the spatial relation between a lesion inside the liver, the liver, the vascular systems surrounding the lesion, the bones surrounding the liver, the intestines, the diaphragm, and other structures that influence the energy distribution or that must not be harmed during an ablation therapy.

In this document ablation is the thermal destruction of biological tissue by means of introducing additional energy into the tissue or by means of extracting energy from the tissue.

The ablation element is a physical device, which is placed, in some embodiments, interstitially inside the tissue in order to achieve the introduction of energy into the tissue or to achieve the extraction of energy from the tissue. For example, in the case of radio-frequency ablation, the ablation element is a needle-shaped probe containing at least one electrode which is connected to an electric generator. In the case of cryo-ablation, the ablation element is a cryo probe, providing a cooling or freezing of the tissue.

In some embodiments, the ablation element setting unit comprises a graphical user interface which allows arranging a graphical model of the ablation element within the segmented image data set on a display unit. The graphical model of the ablation element has an elongated shape, in particular, the shape of the real ablation element, wherein a user can set a desired position and orientation of the graphical model within the segmented image data set, for example, by using input means like a keyboard, a computer mouse or a computer pen.

In particular, the graphical model representing the ablation element can consist of geometric primitives, such as a cylinder with a cone as tip. There exist several possibilities for the user to set a desired position and orientation of the graphical model of the ablation element within the segmented image data set: one possibility for example is to use one mouse click to set the peak of the graphical model of the ablation element and to use a second mouse click to set a point on the shaft of the graphical model of the ablation element. Moreover, while the mouse button is held, the graphical model of the ablation element can be moved and rotated. A further option is to directly enter the coordinates and the orientation of the graphical model of the ablation element via the keyboard. Other input options can be similarly incorporated.

In one embodiment, the model ablation regions, which are stored in the model ablation region storing unit, are determined by solving linear or non-linear equations indicative of assumed or known material properties (e.g., thermal and physical conductivities) of the object of interest and of the environment of the object of interest for determining an energy distribution depending on the spatial relationship and by determining a region, in which the determined energy distribution exceeds a threshold, as model ablation region. A non-linearity of the equations considers material parameters of the materials of the object of interest and of the environment of the object of interest which change with the state or the temperature of the object of interest and/or of the environment of the object of interest. A state of the object of interest and/or of the environment of the object is, for example, the coagulation state, the protein composition, the water content, et cetera. For example, a non-linearity of the equations considers the thermal conductivity, which changes with the temperature. The energy distribution is determined by the Bioheat-Transfer-Equation coupled with another equation, which determines the energy delivered by the model ablation element, e.g., the electrostatic equation in case of radiofrequency ablation. The model energy influencing element is treated as part of the Bioheat-Transfer-Equation either as an energy source/sink term, as a transport term, as a diffusion term, or as boundary conditions for the energy or the energy flux. Several physical factors, i.e., material properties, can be considered, which influence the energy distribution, such as the electrical and thermal conductivity of the tissue, the density and heat capacity of the tissue, as well as the relative perfusion rate. Also phase changes, such as the vaporization of water can be accounted for. Furthermore, for example, the so-called Arrheniusformalism can be used to calculate the region which is considered as destroyed, i.e., to calculate a model ablation region (see e.g., I. Altrogge et al.: Multi-Scale Optimization of the Probe Placement for Radio-Frequency Ablation, Acad. Rad. 14(11), pp. 1310-1324, 2007, and T. Kröoger et al.: Numerical Simulation of Radio Frequency Ablation with State Dependent Material Parameters, Lecture Notes in Computer Science, 4191, pp. 380-388, 2006).

A more detailed description of the calculation of the energy distribution is described in, for example, the above mentioned article by Wood et al., in the article "Thermal modeling of lesion growth with radiofrequency ablation devices", Isaac A. Chang and Uyen D. Nguyen, BioMedical Engineering, OnLine, 3:27, published 6 Aug. 2004, in the article "Multi-Scale Optimization of the Probe Placement for Radio-Frequency Ablation", Altrogge, Inga; Preusser, Tobias; Kroeger, Tim; Bueskens, Christof; Pereira, Philippe L.; Schmidt, Diethard; Peitgen, Heinz-Otto, Academic Radiology 14,11 pages 1310-1324, published 2007 and in the article "Numerical Simulation of Radio Frequency Ablation with State Dependent Material Parameters in Three Space Dimensions", Kroeger, Tim; Altrogge, Inga; Preusser, Tobias; Pereira, Philippe L.; Schmidt, Diethard; Weihusen, Andreas; Peitgen, Heinz-Otto, Lecture Notes on Computer Science 4191, pages 380-388, published 2006; which are herewith incorporated by reference in their entireties.

In some embodiments, the energy distribution is a temperature distribution, wherein, if the ablation should be performed by heating the object of interest, the model ablation element is regarded as a heat source and the model energy influencing element is regarded as a heat sink. If the ablation procedure should be performed by cooling the object of interest, i.e. if the ablation procedure is a cryoablation procedure, the model ablation element is regarded as a heat sink and the model energy influencing element is regarded as a heat source.

In some embodiments, the determined model ablation regions are stored in a look-up table (LUT) in the model ablation region storing unit. The at least one energy influencing element is a vessel like a blood vessel. The energy influencing element can also be another element, which influences the energy distribution, for example, a metal element within a person like a metal element of a prosthesis.

The model ablation region retrieving unit can be adapted to retrieve several model ablation regions which correspond to different combinations of locations on or within the ablation element and locations on or within the at least one energy influencing element. The ablated object region determining unit can then be adapted to determine at least one of a) an ablated object region of the object being located within at least one of the retrieved model ablation regions and b) a non-ablated object region of the object being located outside of all of the retrieved model ablation regions.

In the context of this description, an ablated object region shall mean a region of the object of interest which would be ablated if the ablation element would be used in a therapy for ablating the object with the parameters set by the ablation element setting unit. These parameters are at least the orientation and the position of the ablation element with respect to the provided geometrical representation. The non-ablated object region is a region of the object, which would not be ablated by the ablation element, if the parameters set by the ablation element setting unit would be used in a therapy.

A model ablation element is a possibly idealized representation of the ablation element, which mathematically models the real ablation element, and which can be used in the linear or non-linear equations for determining the model ablation regions. For example, in the case of radio-frequency ablation the model ablation element can be a tube or a cylinder with a polygonal cross section.

A model energy influencing element is a possibly idealized representation of the energy influencing element, which mathematically models the real energy influencing element, and which can be used in the linear or non-linear equations for determining the model ablation regions. For example, in the case the energy influencing element is a blood vessel, a model energy influencing element can be a tube or a cylinder with a polygonal cross section, with finite or infinite length, possibly comprising furcations.

In some embodiments,
  the geometrical representation providing unit is adapted to provide a geometrical representation of a blood vessel being the at least one energy influencing element and of a spatial relationship between the object of interest and the blood vessel,
  the model ablation region storing unit is adapted to store model ablation regions depending on a spatial relationship between a model blood vessel being the model energy influencing element and the model ablation element,
  the model ablation region retrieving unit is adapted to retrieve a model ablation region, which corresponds to the spatial relationship between the ablation element in the set orientation and in the set position and the blood vessel represented by the provided geometrical representation, from the model ablation region storing unit.

This allows fast and accurately determining whether the object of interest, which is a tumor or metastasis, will be completely ablated, if a blood vessel is present in the environment of the object of interest.

In some embodiments,
  the geometrical representation providing unit is adapted to provide a geometrical representation of a vessel tree and of a spatial relationship between the vessel tree and the object of interest,
  the model ablation region storing unit is adapted to store model ablation regions depending on a spatial relationship between a model vessel section being a model energy influencing element and the model ablation element,
  the model ablation region retrieving unit is adapted to divide the vessel tree in vessel sections and to retrieve for each combination of vessel section and set orientation and position of the ablation element a model ablation region, which corresponds to the spatial relationship between the ablation element in the set orientation and in the set position and the vessel section of the respective combination, from the model ablation region storing unit,
  the ablated object region determining unit is adapted to determine at least one of a) an ablated object region of the object of interest and b) a non-ablated object region of the object of interest depending on the retrieved model ablation regions.

In some embodiments, the vessel sections are linear vessel sections.

The indefinite article "a" or "an" does not exclude a plurality. For example, the geometrical representation providing unit can be adapted to provide a geometrical representation of one or several vessel trees and of a spatial relationship between the one or several vessel trees and the object of interest. In particular, if the object of interest is located within or close to a liver, the geometrical representation providing unit can be adapted to provide a geometrical representation of the three vessel trees of the liver and of a spatial relationship between these three vessel trees and the object of interest.

In some embodiments, the ablated object determining unit is adapted to determine at least one of a) an ablated object region of the object of interest being located at least within one of the retrieved model ablation regions and b) a non-ablated object region of the object of interest being located outside of each of the retrieved model ablation regions.

This allows accurately determining the influence of a vessel tree, i.e., one or several vessel trees, on an ablation process with low computational costs, even if the vessel tree has a complicated structure. If the ablated object region and the non-ablated object region are determined in this way, it is not necessary to store ablation regions in the ablation region storing unit, which have been determined by considering different spatial relationships between a complicated vessel structure and an ablation element. In this case, the ablation regions are predetermined for simple spatial relationships between a vessel section and an ablation element, wherein these predetermined ablation regions can be used later during an actual ablated object region determining procedure for determining whether the object of interest would be completely ablated under consideration of the vessel structure.

The model ablation region storing unit may be adapted to store model ablation regions depending on a distance between a model vessel section being a model energy influencing element and the model ablation element.

In particular, in some embodiments, the model ablation region storing unit is adapted to store model ablation regions depending on the distance between a model vessel section and the model ablation element only. If it is assumed that the influence of the diameter, of the kind of blood vessel and of the flow velocity on the energy distribution is relatively small in comparison to the influence of the distance between the ablation element and the vessel section, a consideration of only this distance simplifies the predetermination of the model ablation regions and the corresponding retrieving during an actual ablated object region determining procedure, without significantly reducing the accuracy of determining whether the object of interest will be ablated completely.

In some embodiments, the model ablation region storing unit is adapted to store model ablation regions depending on variations of the distance only, if the at least one model energy influencing element is a model vessel, if the diameter of the model vessel is above a predefined threshold and if the flow velocity within the model vessel is above a further predefined threshold. These thresholds can be determined by measurements, which measure the influence on a model ablation region if the diameter of a vessel and the flow velocity within the vessel are modified.

The model ablation region storing unit can be adapted to store the model ablation regions not only depending on a spatial relationship between the model ablation element and the at least one model energy influencing element, in particular, depending on a distance between the model ablation element and the at least one model energy influencing element. In addition, the model ablation regions can be stored depending on further parameters like the shape of the model ablation element and/or the at least one model energy influencing element, in particular, if the model ablation element and/or the at least one model energy influencing element are cylindrical, the diameter of the cylindrical shape, if the at least one model energy influencing element is a model vessel, the diameter of the model vessel and/or the flow velocity within the model vessel. Other quantities on which the model ablation regions stored by the model ablation region storing unit can depend are in particular:

- the temperature of the model ablation element and/or the at least one model energy influencing element;
- the number of model ablation elements and/or model energy influencing elements;
- the configuration of the model ablation element, in particular, if the model ablation element consists of a radiofrequency applicator that is connected to a radiofrequency generator, the power set up at the generator control unit and the way in which the generator reacts to tissue impedance changes;
- a set of material properties of the surrounding matter inside which the at least one model energy influencing element and the object of interest are located, in particular, if the surrounding matter is human liver parenchyma, its electric conductivity, thermal conductivity, heat capacity, density, and blood perfusion rate;
- the type of the model energy influencing element, if model energy influencing elements of different types are of interest, in particular, if the model energy influencing elements are blood vessels in the human liver, either of a portal vein, a hepatic vein, or a hepatic artery.

In some embodiments, the model ablation region storing unit is adapted to store model ablation regions, which have been determined by solving biophysical equations describing an energy distribution of the object of interest and of the environment of the object of interest.

In some embodiments, the model ablation region storing unit is adapted to store model ablation regions, which have been determined experimentally.

In some embodiments,—the model ablation region storing unit is adapted to store at least two types of model ablation regions, a first type of model ablation region defining a model ablation region considering the influence of the at least one model energy influencing element on the model ablation region and a second type of model ablation region not considering the influence of the at least one model energy influencing element on the model ablation region,

- the model ablation region retrieving unit is adapted to retrieve a first model ablation region of the first type and a second model ablation region of the second type depending on the spatial relationship between the ablation element in the set orientation and in the set position and the at least one energy influencing element represented by the provided geometrical representation,
- the ablated object region determining unit is adapted to determine at least one of a) an ablated object region of the object of interest being located within the retrieved first model ablation region, b) a first non-ablated object region of the object of interest being located within the second model ablation region and outside the first model ablation region, and c) a second non-ablated object region of the object of interest being located outside the first model ablation region and outside the second model ablation region.

The ablated object region determining apparatus may comprise a visualization unit being adapted to visualize the ablated object region, the first non-ablated object region and the second non-ablated object region differently.

This allows visualizing three regions of the object of interest, an ablated object region, which indicates regions which will be destroyed, a first non-ablated object region, which would be destroyed, if the at least one energy influencing element would not be present, but which will not be destroyed, because the at least one energy influencing element is present, and a second non-ablated object region which will not be destroyed, even if the at least one energy influencing element would not be present, because of the relatively large distance to the ablation element.

The visualization of the first non-ablated object region can help the physician to decide whether it is reasonable to perform additional steps that will weaken or avoid the influence of the at least one energy influencing element. If the at least one energy influencing element is a vascular system in the human liver, such an additional step could in particular be a Pringle manoeuvre or a chemoembolization of the particular vessel.

The visualization of the second non-ablated object region can help the physician to decide whether a second ablation element should be used or in the particular case in which the ablation element consists of a radiofrequency applicator which is connected to a radiofrequency generator whether the power set up at the radiofrequency generator must be increased.

Further, the ablated object region determining unit may be adapted to determine at least one of a) an ablated object region and b) a non-ablated object region on an outer surface of the object of interest only.

Since at least one of an ablated object region and of a non-ablated object region, in particular, of a first non-ablated object region and of a second non-ablated object region, are determined on the outer surface of the object only, the computational costs needed for determining at least one of the ablated object region and of the non-ablated object region are reduced.

In some embodiments, the display unit only shows the outer surface of the object. The visualization unit is therefore adapted to visualize the ablated object region and the non-ablated object region, in particular, the first non-ablated object region and the second non-ablated object region, by visualizing the corresponding areas on the outer surface of the object differently, for example, by coloring the outer surface of the object differently. This reduces the computational costs for visualizing at least one of the ablated object region of the object and of the non-ablated object region of the object differently.

In some embodiments,—the model ablation region storing unit is adapted to store two-dimensional model ablation regions depending on a distance between the at least one model energy influencing element and the model ablation element, the model ablation region retrieving unit is adapted to retrieve two-dimensional model ablation regions corresponding to a group of planes defined by locations on or within the object of interest, locations on or within the at least one energy influencing element, and locations on or within the ablation element, wherein the two-dimensional model ablation regions within these planes depend on the distance between the location on or within the at least one energy influencing element and the location on or within the ablation element, the ablated object region determining unit is adapted to determine at least one of a) the ablated object region of the object and b) the non-ablated object region of the object depending on the retrieved two-dimensional model ablation regions.

In some embodiments, the ablated object region determining unit is adapted to determine at least one of a) the ablated object region of the object comprising locations on or within the object being located within at least one of the retrieved two-dimensional model ablation regions and b) the non-ablated object region of the object comprising locations on or within the object being located outside of all retrieved two-dimensional model ablation regions.

In some embodiments, the model ablation region storing unit is adapted to store at least two types of two-dimensional model ablation regions, a first type of model ablation region defining a model ablation region considering the influence of the at least one model energy influencing element on the model ablation region and a second type of model ablation region not considering the influence of the at least one model energy influencing element on the model ablation region. In this embodiment, the model ablation region retrieving unit is adapted to retrieve two-dimensional model ablation regions of the first type and of the second type corresponding to a group of planes defined by locations on or within the object, locations on or within the at least one model energy influencing element, and locations on or within the model ablation element, wherein the two-dimensional model ablation regions of the first type and of the second type within these planes depend on the distance between the location on or within the at least one model energy influencing element and the location on or within the model ablation element within the respective plane. The ablated object region determining unit is adapted to determine at least one of a) an ablated object region of the object comprising locations on or within the object being located within at least one of the retrieved first model ablation regions, b) a first non-ablated object region of the object comprising locations on or within the object being located within at least one second model ablation region and outside of all retrieved first model ablation regions, and c) a second non-ablated object region of the object comprising locations on or within the object being located outside of all retrieved first model ablation regions and outside of all retrieved second model ablation regions.

In some embodiments,—the model ablation region storing unit is adapted to store two-dimensional model ablation regions depending on a distance between the at least one model energy influencing element and the model ablation element, wherein a border of the respective two-dimensional model ablation region is parameterized by an angle with respect to a line connecting a location on or within the at least one model energy influencing element and a location on or within the model ablation element and an ablation distance between the border of the two-dimensional model ablation region and the location on or within the model ablation element in a direction defined by the angle, the model ablation region retrieving unit and the ablated object region determining unit are adapted to perform following steps for each location on or within the object of interest:

determine for each location on or within the at least one energy influencing element, for each location on or within the ablation element and the location on or within the object a two-dimensional plane defined by these locations, determine for each location on or within the at least one energy influencing element, for each location on or within the ablation element and the location on or within the object an angle within the determined plane as an angle between a line connecting the location on or within the at least one energy influencing element and the location on or within the ablation element within the determined plane and a line connecting the location on or within the ablation element and the location on or within the object within the determined plane, retrieve for each location on or within the at least one energy influencing element, for each location on or within the ablation element and the location on or within the object the ablation distance between the location on or within the ablation element and the border of the model ablation region within the determined plane in the direction of the determined angle, which corresponds to the respective distance between the location on or within the at least one energy influencing element and the location of the ablation element, determine whether the location on or within the object is within an ablated object region or within a non-ablated object region depending on the retrieved ablation distances.

This procedure allows to store model ablation regions in the model ablation region storing unit using a minimal amount of memory, while retrieving, for example, three-dimensional model ablation regions from the model ablation region retrieving unit is still possible as has been described above.

In another aspect, a model ablation region determining apparatus for determining model ablation regions is presented, wherein the model ablation region determining apparatus is adapted to determine the model ablation regions depending on a spatial relationship between a model ablation element and at least one model energy influencing element, wherein a model ablation region defines a region which will be ablated given the respective spatial relationship between the model ablation element and the at least one model energy influencing element, store the determined model ablation regions in a model ablation region storing unit.

The model ablation regions can be determined by determining an ablation region using a model of partial differential equations, wherein only one model energy influencing element is present and has a cylindrical shape with circular or polygonal cross-section and is located in the vicinity of the model ablation element. Distances from the center of the ablation element to the boundary of the determined ablation region are determined, wherein this measurement is performed in various directions and generally depends on the direction. These measurements are performed for different spatial relationships between the model ablation element and the at least one model energy influencing element and the resulting distances are stored in the model ablation region storing unit for storing the model ablation regions.

The partial differential equations, which can be used for determining an ablation region, are partial differential equations described in the above mentioned articles.

In another aspect, an arranging apparatus for arranging an ablation element within an object of interest is presented, wherein the arranging apparatus comprises:

an ablation planning device comprising an ablated object region determining apparatus as defined in claim 1 for planning a position and orientation of the ablation element such that a desired ablated object region is determined, an ablation element navigation unit for navigating the ablation element to the planned position in the planned orientation.

This allows placing the ablation element within a person or within an animal in accordance with the planned position and orientation of the ablation element.

In some embodiments, the arranging apparatus further comprises:

an actual object geometry data set providing unit for providing an actual object geometry data set showing the object, an actual ablation element geometry data set providing unit for providing an actual ablation element geometry data set showing the ablation element, an actual position and orientation determination unit for determining the actual position and orientation of the ablation element within the provided actual ablation element geometry data set and/or for determining the actual position of the object within the provided actual ablation element geometry data set, a comparing unit for comparing the determined actual position and orientation of the ablation element with the planned position and orientation of the ablation element, wherein the ablation element navigation unit is adapted to indicate the distance and the direction from the actual position in the actual orientation to the planned position in the planned orientation, if a deviation of the actual orientation from the planned orientation is larger than an orientation threshold and/or if a deviation of the actual position from the planned position is larger than a position threshold.

For the physician this allows performing the ablation with the planned position and the planned orientation of the ablation element also on base of a geometry description, which is not the original one used for the planning. It allows identifying the angle of the trajectory of penetration of a patient with the ablation element, which leads to the planned orientation and to the planned position of the ablation element. Also it allows correcting the orientation of the trajectory of penetration of a patient with the ablation element if, for example, a first step of the penetration procedure for inserting the ablation element to a planned position in the planned orientation does not yield the planned orientation or does not lead to the planned placement. For a correction of the penetration trajectory the comparing unit indicates the corrected angles of penetration that lead to the planned placement and the planned orientation. This improves the accuracy of arranging the ablation element in accordance with the planned orientation and position of the ablation element.

In another aspect, an ablated object region determining method for determining an ablated object region for ablating an object of interest is presented, wherein the ablated object region determining method comprises following steps:

providing a geometrical representation of the object of interest, of at least one energy influencing element and of a spatial relationship between the object of interest and the at least one energy influencing element, setting an orientation and position of the ablation element with respect to the provided geometrical representation, retrieving a model ablation region, which corresponds to the spatial relationship between the ablation element in the set orientation and in the set position and the at least one energy influencing element represented by the provided geometrical representation, from a model ablation region storing unit in which model ablation regions are stored depending on a spatial relationship between a model ablation element and at least one model energy influencing element, wherein a model ablation region defines a region which will be ablated given a respective spatial relationship between the model ablation element and the at least one model energy influencing element, determining at least one of a) an ablated object region of the object of interest being located within the retrieved model ablation region and b) a non-ablated object region of the object of interest being located outside the retrieved model ablation region.

In another aspect, a model ablation region determining method for determining model ablation regions is presented, wherein the model ablation region determining method comprises following steps:

determining the model ablation regions depending on a spatial relationship between a model ablation element and at least one model energy influencing element, wherein a model ablation region defines a region which will be ablated given the respective spatial relationship between the model ablation element and the at least one model energy influencing element, storing the determined model ablation regions in a model ablation region storing unit.

In another aspect, an arranging method for arranging an ablation element within an object is presented, wherein the arranging method comprises following steps:

planning a position and orientation of the ablation element depending on an ablated object region of the object of interest determined by the ablated object region determining method, navigating the ablation element to the planned position in the planned orientation.

In another aspect, an ablated object region determining computer program for determining an ablated object region for ablating an object is presented and stored in a computer storage device or computer-readable medium such as a computer memory, wherein the computer program comprising program code or other instruction means for causing an ablated object region determining apparatus as defined in claim 1 to carry out the steps of the ablated object region determining method, when the computer program is run on a computer with a computer processor controlling the ablated object region determining apparatus.

In another aspect, a model ablation region determining computer program for determining model ablation regions is presented and stored in a computer storage device or computer-readable medium such as a computer memory, wherein the computer program comprises program code or other instruction means for causing a model ablation region determining apparatus to carry out the steps of the model ablation region determining method when the computer program is run on a computer with a computer processor controlling the model ablation region determining apparatus.

In another aspect, an arranging computer program for automatically arranging an ablation element within an object is presented and stored in a computer storage device or computer-readable medium such as a computer memory or storage device, wherein the computer program comprises program code or other instruction means for causing an arranging apparatus to carry out the steps of the arranging method, when the computer program is run on a computer with a computer processor controlling the arranging apparatus.

The ablated object region determining apparatus of claim 1, the model ablation region determination apparatus, the arranging apparatus, the ablated object region determining method, the model ablation region determination method, the arranging method, the ablated object region determining computer program, the model ablation region determination computer program and the arranging computer program may have similar and/or identical embodiments as defined in the dependent claims.

Embodiments can also be any combination of the dependent claims with the respective independent claims.

DETAILED DESCRIPTION

Figure 1:
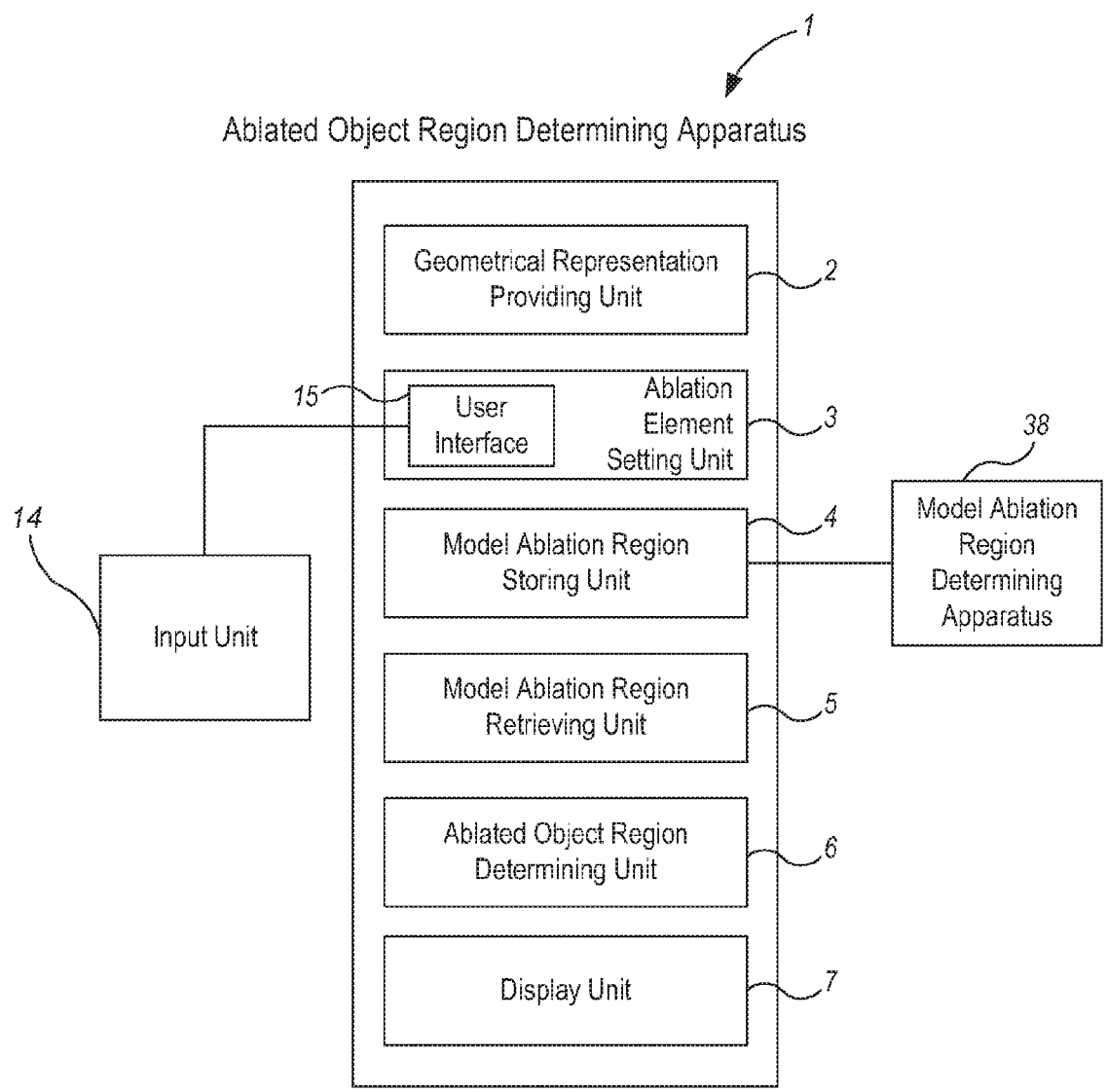
FIG. 1 shows schematically and exemplarily an embodiment of an ablated object region determining apparatus.
Figure 2:
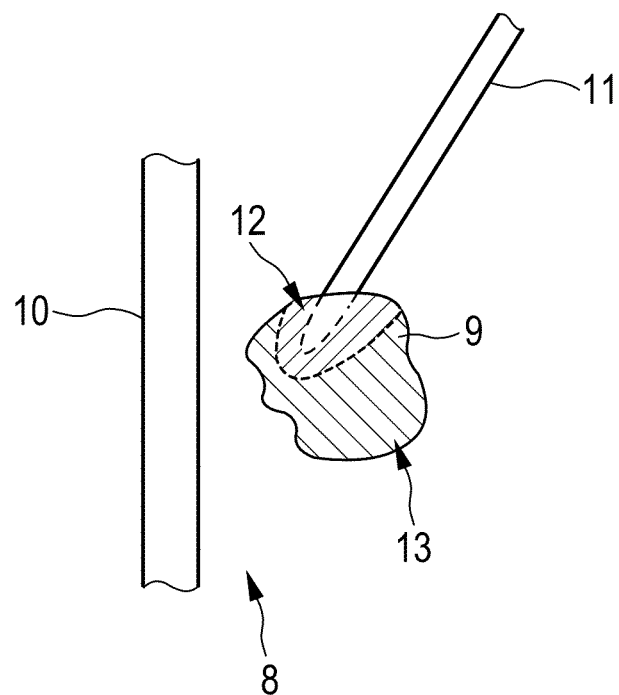
FIG. 2 shows schematically and exemplarily a graphical representation of an ablation element, wherein the orientation and position of the graphical representation has been set with respect to a geometrical representation of an object of interest and an energy influencing element.

FIG. 1 shows schematically and exemplarily an ablated object region determining apparatus 1 for determining an ablated object region for ablating an object of interest. The ablated object region determining apparatus 1 comprises a geometrical representation providing unit 2 for providing a geometrical representation of i) the object of interest, ii) at least one energy influencing element and iii) a spatial relationship between the object of interest and the at least one energy influencing element. Such a geometrical representation 8 is schematically and exemplarily shown in FIG. 2. The geometrical representation 8 represents the object of interest 9, the at least one energy influencing element 10 and the spatial relationship between the object of interest 9 and the at least one energy influencing element 10.

The ablated object region determining apparatus 1 further comprises an ablation element setting unit 3 for allowing a user to set an orientation and position of an ablation element 11, i.e. of a graphical model 11 of an ablation element, with respect to the provided geometrical representation 8. The ablation element setting unit 3 comprises a graphical user interface 15 which allows arranging a graphical model 11 of the ablation element with respect to the geometrical representation 8 on a display unit 7 of the ablated object region determining apparatus 1. The graphical model of the ablation element 11 has an elongated shape, in particular, the shape of the real ablation element, wherein a user can set a desired position and orientation of the graphical model with respect to the geometrical representation 8 by using an input unit 14 like a keyboard, a computer mouse or a computer pen.

Figure 3:
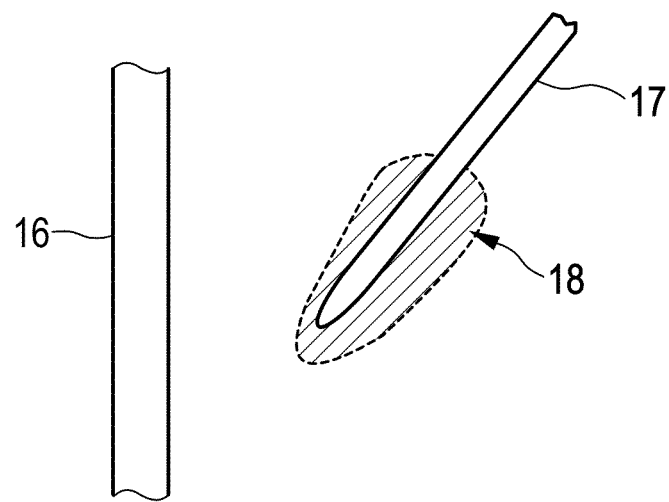
FIG. 3 shows schematically and exemplarily a model ablation element, a model energy influencing element and a determined model ablation region.

The ablated object region determining apparatus 1 further comprises a model ablation region storing unit 4 in which model ablation regions are stored depending on a spatial relationship between a model ablation element and at least one model energy influencing element, wherein a model ablation region defines a region, which will be ablated given a respective spatial relationship between the model ablation element and the at least one energy influencing element. A model energy influencing element 16, a model ablation element 17 and a model ablation region 18 are schematically and exemplarily shown in FIG. 3.

The ablated object region determining apparatus 1 further includes a model ablation region retrieving unit 5 for retrieving a model ablation region 18 which corresponds to the spatial relationship between the ablation element 11 in the set orientation and in the set position and the at least one energy influencing element 10 represented by the provided geometrical representation 8, from the model ablation region storing unit 4.

The ablated object region determining apparatus 1 further comprises an ablated object region determining unit 6 for determining at least one of a) an ablated object region 12 of the object of interest 9 being located within the retrieved model ablation region 18 and b) a non-ablated object region 13 of the object of interest 9 being located outside the retrieved model ablation region 18.

The display unit 7 may be adapted to visualize the ablated object region 12 of the object 9 and the non-ablated object region 13 of the object 9 differently, for example, by different colors and/or intensities.

The ablated object region determining apparatus allows to simulate an ablation procedure, before the ablation procedure is actually performed. That means, before the ablation procedure is actually performed, the ablated object region determining unit can determine an ablated object region 12 and/or a non-ablated object region 13, which are visualized on the display unit 7 and which can be used by a user like a physician for planning a following real ablation procedure. Before the actual ablation procedure is performed, the physician can see which part of the object of interest 9 would be ablated and which part of the object of interest 9 would not be ablated if the set position and the set orientation is used for the real therapy. Since the required model ablation regions 18 are retrieved from the model ablation region storing unit 4, i.e. since these model ablation regions 18 do not have to be calculated, the ablated object region 12 and the non-ablated object region 13 can be determined and visualized very fast.

In this example embodiment, the geometrical representation providing unit 2 is an image data set providing unit for providing a segmented image data set representing the object of interest 9, the energy influencing element 10 and the spatial relationship between the object of interest 9 and the energy influencing element 10. Thus, in this embodiment the segmented image data set provides the geometrical representation. The medical image data set may be a medical image data set showing the whole body or a part of the body of a person or of an animal. For example, the image data set can be an image data set showing an organ like the lung or the liver.

The image data set can be generated by an imaging modality like a computed tomography imaging system, a magnetic resonance imaging system, a nuclear medicine imaging system or an ultrasound imaging system. The image data set providing unit can comprise at least one of the previously mentioned imaging systems for generating the image data set and a segmentation unit for segmenting at least the object of interest and the at least one energy influencing element within the image data set.

The geometrical representation providing unit 2 can also be a storing unit in which the geometrical representation, which can be a segmented image data set, is stored. The geometrical representation providing unit 2 can also be a receiving unit for receiving the geometrical representation and for providing the received geometrical representation to the ablation element setting unit 3. The receiving unit can be adapted for receiving the segmented image data set via a wired or wireless data link.

The geometrical representation providing unit 2 and/or the ablation element setting unit 3 can also be adapted to provide a geometrical description of the ablation element 11 and/or the energy influencing element 10, respectively, as one or several of the following:
  one or several cylinders having circular or polygonal cross-section, parameterized by the radius, height, position, and orientation of the one or several cylinders;
  a number of polyhedra that make up a closed surface, where the polyhedra are for example parameterized by the coordinates of their vertices;
  an implicit function representation, that is, a real-valued function on a three-dimensional set that takes values of a certain sign inside the ablation element (or inside the at least one energy influencing element, respectively) and values of the opposite sign outside the ablation element (or inside the at least one energy influencing element, respectively).

In addition to providing the geometrical representation 8 of the object of interest 9 and the energy influencing element 10, the geometrical representation providing unit 2 can be adapted to additionally provide the geometry and the spatial relation of structures in a body of a person or of an animal, which are in the vicinity of the object of interest 9. In such an embodiment, the geometrical representation providing unit 2 may describe the geometry of and the spatial relation between a lesion being the object of interest inside the liver, the liver, the vascular systems surrounding the lesion, the bones surrounding the liver, the intestines, the diaphragm, and other structures that influence the energy distribution or that must not be harmed during an ablation therapy.

In this example embodiment, the object of interest 9 is a lesion and the energy influencing element 10 is a blood vessel. For example, the object of interest can be a metastasis or a primary tumor. Moreover, in this embodiment the ablation element being represented by the graphical model 11 is a radio-frequency ablation element being a needle-shaped probe containing at least one electrode which is connected to an electric generator. In other embodiments, the ablation element can have another shape and/or can be adapted to introduce another kind of energy into the object of interest 9. For example, the ablation element can be a cryo probe for providing a cooling or freezing of the object of interest for performing a cryo-ablation procedure.

In this example embodiment, the model ablation regions 18, which are stored in the model ablation region storing unit 4, have been determined by solving linear or non-linear equations indicative of assumed or known material properties (e.g. thermal and electrical conductivity) of the object of interest 9 and of the environment of the object of interest 9 for determining an energy distribution depending on the spatial relationship between the model ablation element 17 and the model energy influencing element 16 and by determining a region 18, in which the determined energy distribution exceeds a threshold, as model ablation region 18. The non-linearity of the equations considers material parameters of the materials of the object of interest 9 and of the environment of the object of interest 9, which change with the temperature or other states of the object of interest 9 and/or of the environment of the object of interest 9. A state of the object of interest 9 and/or of the environment of the object 9 is, for example, the coagulation state, the protein composition, the water content, et cetera. In this embodiment the non-linearity of the equations considers the thermal conductivity and in the case of radiofrequency ablation also the electric conductivity, which change with the temperature and the other states of the object of interest and its environment. Moreover, in this embodiment the energy distribution is determined by the Bioheat-Transfer-Equation coupled with another equation which determines the energy delivered by the model ablation element, for example, the electrostatic equation in case of radiofrequency ablation. The model energy influencing element 16 is treated as part of the Bioheat-Transfer-Equation either as an energy source/sink term, as a transport term, as a diffusion term, or as boundary conditions for the energy of the energy flux. Several physical factors, i.e. material properties, are considered which influence the energy distribution such as the electrical and thermal conductivity of the tissue, the density and heat capacity of the tissue and the relative perfusion rate. Also phase changes like the vaporization of water can be accounted for. A more detailed description of such a determination of the model ablation region 18 is described in more detail in the above mentioned articles, which are incorporated by reference.

In this example embodiment, the energy distribution is a temperature distribution, wherein the model ablation element 17 is regarded as a heat source and the model energy influencing element 16 is regarded as a heat sink. If, in another embodiment, the ablation procedure should be performed by cooling the object of interest 9, the model ablation element 17 is regarded as a heat sink and the model energy influencing element 16 is regarded a heat source.

The determined model ablation regions are stored in a lookup table in the model ablation region storing unit 4. The stored model ablation regions have been determined for different spatial relationships between the model ablation element 17 and the energy influencing element 16. Moreover, in an embodiment for the same spatial relationship between the model ablation element 17 and the model energy influencing 16 several model ablation regions can be stored in the model ablation region storing unit 4, which correspond to different combinations of locations on or within the model ablation element 7 and locations on or within the model energy influencing element 16, wherein the model ablation region retrieving unit 5 is adapted to retrieve these several model ablation regions, i.e. the ablated object region determining unit 6 is then adapted to determine at least one of a) an ablated object region 12 of the object 9 being located within at least one of the retrieved model ablation regions and b) a non-ablated objected region 13 of the object 9 being located outside of all of the retrieved model ablation regions.

Figure 4:
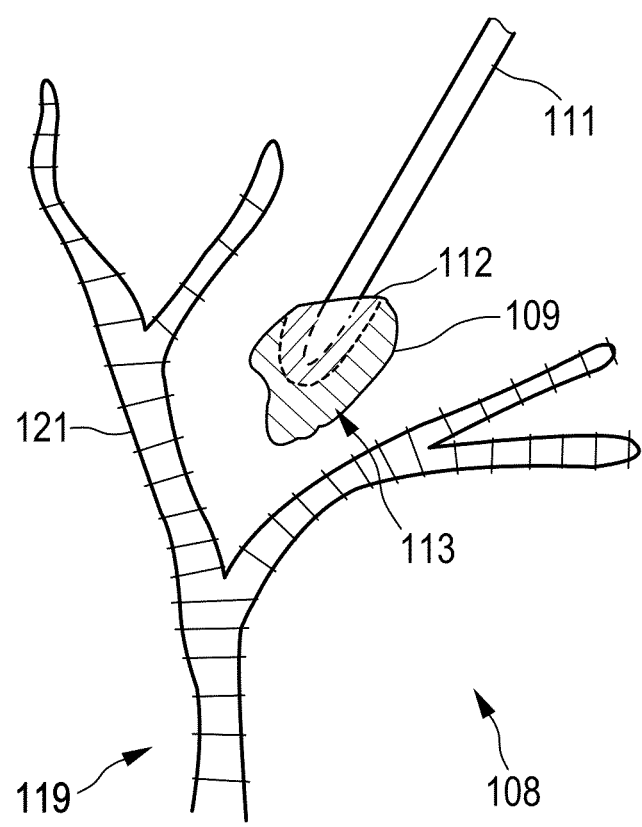
FIG. 4 shows schematically and exemplarily a graphical representation of an ablation element whose orientation and position has been set with respect to a geometrical representation of a vessel tree and an object of interest.

The energy influencing element can also be a vessel tree 119 which is schematically and exemplarily shown in FIG. 4.

FIG. 4 shows schematically and exemplarily a geometrical representation 108 representing the vessel tree 119, the object of interest 109 and a spatial relationship between the vessel tree 119 and the object of interest 109. Also this geometrical representation can be provided by the geometrical representation providing unit 2. The vessel tree 119 can be divided into vessel sections 121.

Figure 5:
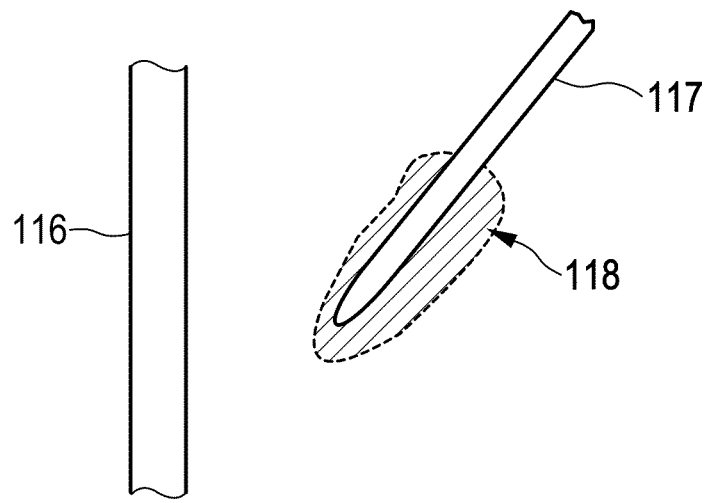
FIG. 5 shows schematically and exemplarily a model vessel section being a model energy influencing element, a model ablation element, and a model ablation region of a first type.

In this example embodiment, the model ablation region storing unit 4 is adapted to store model ablation regions 118 depending on a spatial relationship between a model vessel section 116 being a model energy influencing element and a model ablation element 117. The model vessel section 116, the model ablation element 117 and the model ablation region 118 are schematically and exemplarily shown in FIG. 5.

The model ablation region retrieving unit 5 is adapted to divide the vessel tree 119 in the vessel sections 121 and to retrieve for each combination of vessel section 121 and set orientation and position of the ablation element 111 a model ablation region 118 which corresponds to the spatial relationship between the ablation element 111 in the set orientation and in the set position and the vessel section 121 of the respective combination, from the model ablation region storing unit 4. The ablated object region determining unit is adapted to determine an ablated object region 112 of the object of interest 109 being located within the retrieved model ablation region 118 and b) a non-ablated object region 113 of the object of interest 109 being located outside of the retrieved model ablation region 118. The ablated object region 112 and the non-ablated object region 113 are visualized differently on the display unit 7.

In this example embodiment, the vessel sections 121 and the model vessel sections 116 are linear sections.

The model ablation region storing unit 4 may be adapted to store model ablation regions depending on a distance between a model vessel section 116 being a model energy influencing element and the model ablation element 117. In particular, the model ablation region storing unit 4 can be adapted to store model ablation regions depending on a distance between a model vessel section 116 and a model ablation element 117 only. It is further preferred that the model ablation region storing unit 4 is adapted to store model ablation regions depending on the distance only, if the model energy influencing element is a model vessel or model vessel section 116, if a diameter of the model vessel or model vessel section 116 is above a predefined threshold and if the flow velocity within the model vessel or model vessel section 116 is above a further predefined threshold. These thresholds are determined by measurements which measures the influence on a model ablation region, if the diameter of a vessel and the flow velocity within the vessel are modified.

The model ablation region storing unit 4 can also be adapted to store the model ablation regions not only depending on a spatial relationship between the model ablation element and the at least one model energy influencing element, in particular, depending on a distance between the model ablation element and the at least one model energy influencing element. In addition, the model ablation regions can be stored depending on further parameters which are mentioned above like the shape of the model ablation element and/or of the at least on model energy influencing element, in particular, if the model ablation element and/or the at least one model energy influencing element are cylindrical, on the diameter of the cylindrical shape, and/or, if the at least one model energy influencing element is a model vessel, on the diameter of the model vessel and/or the flow velocity within the model vessel.

Although in the above mentioned example embodiments the model ablation regions stored in the model ablation region storing unit 4 have been determined by solving biophysical equations like the Bioheat-Transfer-equation, in other example embodiments, the model ablation regions can have been determined in another way, for example, experimentally.

Figure 6:
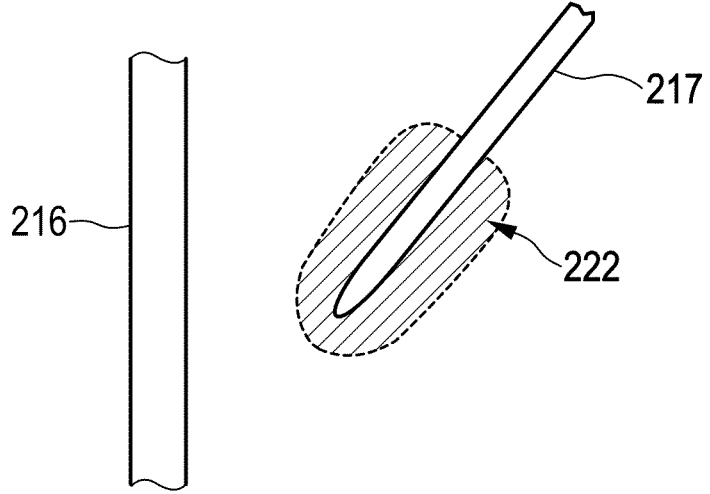
FIG. 6 shows schematically and exemplarily a model vessel being a model energy influencing element, a model ablation element and a model ablation region of a second type.

In a further example embodiment, the model ablation region storing unit 5 is adapted to store two types of model ablation regions, a first type of model ablation region 118 defining a model ablation region considering the influence of the model energy influencing element 116 on the model ablation region and a second type of model ablation region 222 not considering the influence of the model energy influencing element 216 on the model ablation region. FIG. 6 shows schematically and exemplarily a second type of model ablation region 222, the model ablation element 217, and the model energy influencing element 216. The first type of model ablation region defining a model ablation region considering the influence of the model energy influencing element corresponds to the model ablation region 18 shown in FIG. 3.

Figure 7:
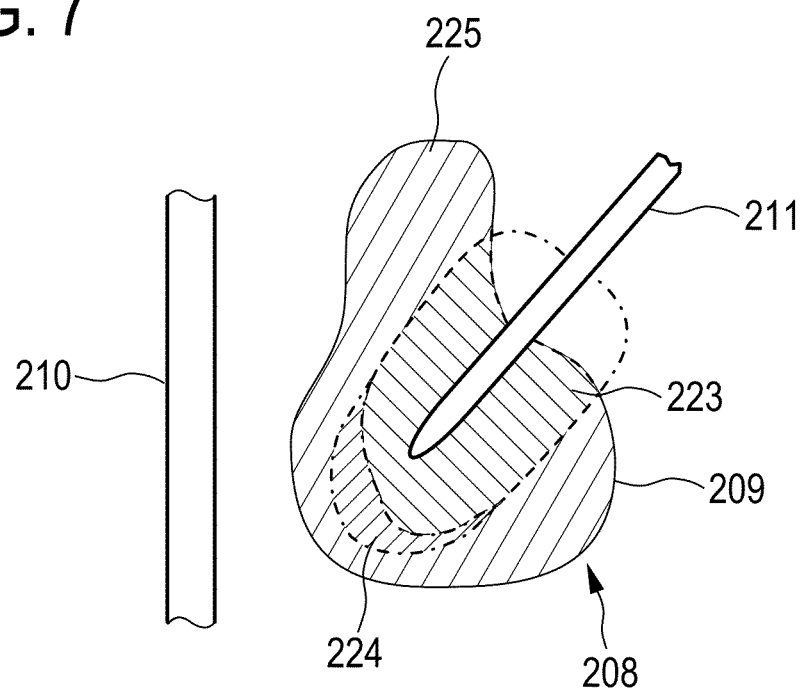
FIG. 7 shows schematically and exemplarily a graphical representation of an ablation element oriented and positioned with respect to a geometrical representation of an energy influencing element and an object of interest.

In this example embodiment, the model ablation region retrieving unit 5 is adapted to retrieve a first model ablation region 118 of the first type and a second model ablation region 222 of the second type depending on the spatial relationship between the ablation element 211 in the set orientation and in the set position and the energy influencing element 210 represented by their provided geometrical representation 208. The geometrical representation 208 representing the ablation element 211, the energy influencing element 210 and the spatial relationship between the ablation element 211 and the energy influencing element 210 are schematically and exemplarily shown in FIG. 7.

Moreover, in this example embodiment the ablated object region determining unit 6 is adapted to determine at least one of a) an ablated object region 223 of the object of interest 209 being located within the retrieved first model ablation region, b) a first non-ablated object region 224 of the object of interest 209 being located within the second model ablation region and outside the first model ablation region, and c) a second non-ablated object region 225 of the object of interest 209 being located outside the first model ablation region and outside the second model ablation region. The display unit 7 is adapted to visualize the ablated object region 223, the first non-ablated object region 224 and the second non-ablated object region 225 differently, in particular, with different colors and/or different intensities.

The ablated object region determining unit 6 may be adapted to determine the ablated object region and the non-ablated object region, in particular, the first non-ablated object region and the second non-ablated object region, on an outer surface of the object of interest only. Moreover, the display unit 7 can be adapted to show the outer surface of the object of interest and the ablated and non-ablated object regions on the outer surface of the object of interest, and not the inside of the object of interest.

In an example embodiment, the model ablation region storing unit 4 is adapted to store two-dimensional model ablation regions 318 depending on a distance between the model energy influencing element and the model ablation element. In this embodiment, the model ablation region retrieving unit 5 is adapted to retrieve two-dimensional model ablation regions 318 corresponding to a group of planes defined by locations 327 on the object of interest 309, locations 326 on the energy influencing element 310 and locations 328 on the ablation element 311, wherein the two-dimensional model ablation regions 318 within these planes depend on the distance between the respective location 326 on the energy influencing element 310 and the respective location 328 on the ablation element 311. The locations are schematically and exemplarily illustrated in FIG. 8.

Figure 8:
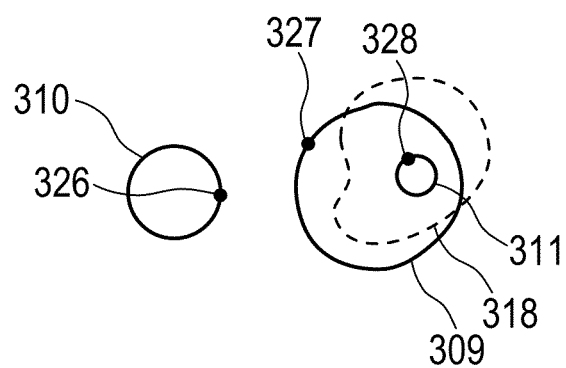
FIG. 8 shows schematically and exemplarily locations on an energy influencing element, on an object of interest, and on an ablation element being used for determining ablated object regions.

In FIG. 8, the location 326 on the energy influencing element 310, the location 327 on the object of interest 309 and the location 328 on the ablation element 311 define a plane, wherein the two-dimensional model ablation region 318 is retrieved from the model ablation region storing unit 4 depending on the distance between the location 326 on the energy influencing element 310 and the location 328 on the ablation element 311. The location 327 on the object of interest 309 is not within the two-dimensional model ablation region 318.

For a location 327 on the object of interest 309 model ablation regions are retrieved for different locations on the energy influencing element 310 and different locations on the ablation element 311. If the location 327 is located within at least one of the ablation regions, the location 327 on the object of interest 309 is assigned to an ablated object region. Otherwise, the location 327 on the object of interest 309 is assigned to a non-ablated object region of the object of interest 309. These assignments are performed for all locations on the object of interest 309. Then, the ablated object region and the non-ablated object region on the object of interest 219 are visualized differently by the display unit 7, in particular, with different colors and/or different intensities. This allows determining and identifying an ablated object region and a non-ablated object region on the object of interest 309 in a three-dimensional configuration, although the model ablation regions stored in the model ablation region storing unit are two-dimensional regions.

The concept of using two-dimensional stored model ablation regions for determining and visualizing an ablated object region and a non-ablated object region in a three-dimensional configuration can also be used, if the model ablation region storing unit includes a first type of two-dimensional model ablation region and a second type of two-dimensional model ablation region. For example, the model ablation region storing unit 4 can be adapted to store a first type of two-dimensional model ablation regions defining model ablation regions considering the influence of the model energy influencing element on the model ablation region and a second type of two-dimensional model ablation regions not considering the influence of the model energy influencing element on the model ablation region. The model ablation region retrieving unit 5 is then adapted to retrieve two-dimensional model ablation regions of the first type and of the second type corresponding to a group of planes defined by locations on the object of interest, on the model energy influencing element, and on the model ablation element, wherein the two-dimensional model ablation regions of the first type and of the second type within these planes depend on the distance between the respective location on the model energy influencing element and the respective location on the model ablation element within the respective plane. The ablated object region determining unit 6 is adapted such that in this case at least one of a) an ablated object region of the object comprising locations on the object being located within at least one of the retrieved first model ablation regions, b) a first non-ablated object region of the object comprising locations on the object being located within at least one second model ablation region and outside of all retrieved first model ablation regions, and c) a second non-ablated object region of the object comprising locations on the object being located outside of all retrieved first model ablation regions and outside of all retrieved second model ablation regions are determined.

Figure 9:
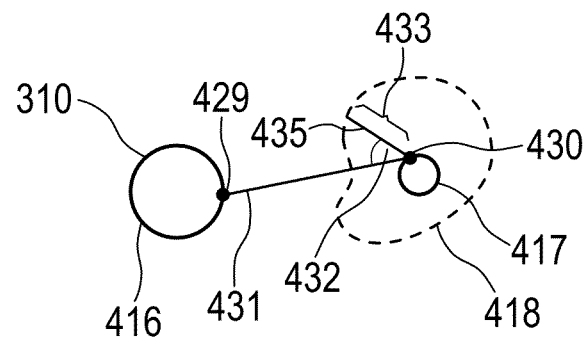
FIG. 9 shows schematically and exemplarily a parameterization of a model ablation region.

In the following an example parameterization of the model ablation regions will be described with reference to FIG. 9.

The model ablation region storing unit 4 may be adapted to store two-dimensional model ablation regions 418 depending on a distance between the energy influencing element 416 and the model ablation element 417. The border of the respective two-dimensional model ablation region 418 is parameterized by an angle 432 with respect to a line 431 connecting a location 429 on the model energy influencing element 416 and a location 430 on the model ablation element 417 and an ablation distance 433 between the border of the two-dimensional ablation region 418 and the location 430 on the model ablation element 417 in a direction defined by the angle 432. Thus, the two-dimensional model ablation regions are stored in the model ablation region storing unit 4 by defining multiple lengths of a vector 435 for different angles 432 between the connection line 431 and the vector 435.

Figure 10:
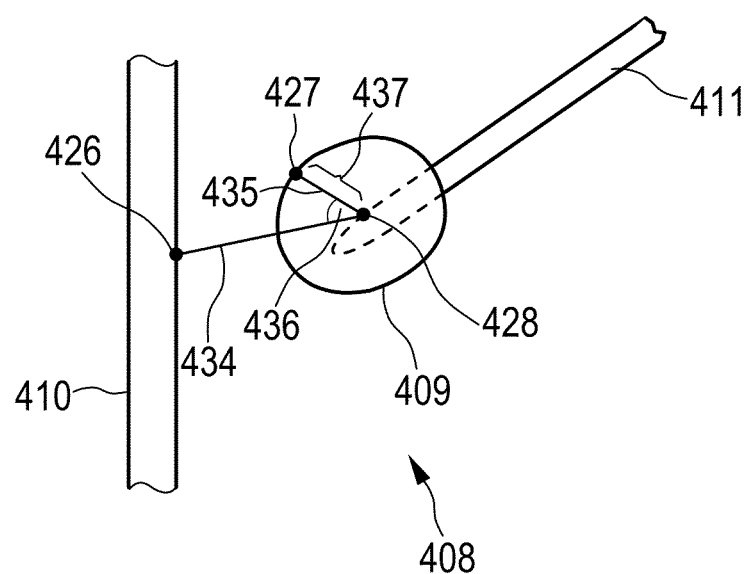
FIG. 10 shows schematically and exemplarily a graphical representation of an ablation element oriented and positioned with respect to a geometrical representation of an object of interest and an energy influencing element.

In the following, example embodiments of the model ablation retrieving unit 5 and the ablated object region determining unit 6, which use the stored ablation distances and angles, are described with reference to FIG. 10.

The model ablation region retrieving unit 5 and the ablated object region determining unit 6 are adapted to perform following steps for each location 427 on the object of interest 409. For each location 426 on the energy influencing element 410, for each location 428 on the ablation element 411 and for the location 427 on the object 409 a two-dimensional plane defined by these locations is determined. Then, for each location 426 on the energy influencing element 410, for each location 428 on the ablation element 411 and for the location 427 on the object 409 an angle 436 within the determined plane is determined as an angle between a line 434 connecting the location 426 on the energy influencing element 410 and the location 428 on the ablation element 411 within the determined plane and a line 435 connecting the location 428 on the ablation element 411 and the location 427 on the object 409 within the determined plane. For each location 426 on the energy influencing element 410, for each location 428 on the ablation element 411 and for the location 427 on the object of interest 409 the ablation distance 437 between the location 428 on the ablation element 411 and the border of the model ablation region within the respective determined plane in the direction of the respective determined angle 436 is retrieved, wherein the ablation distance 437, which has been retrieved for the determined angle 436 and for the locations on the energy influencing element, on the ablation element and on the object, corresponds to the respective distance between the location 426 on the energy influencing element, 410 and the location 428 on the ablation element 411. Then, it is determined whether the location 427 on the object 409 is within an ablated object region or within a non-ablated object region depending on the retrieved ablation distances. In particular, if the respective location 427 on the object 409 is within at least one of the retrieved ablation distances, the location 427 on the object 409 is assigned to the ablated object region, and if the location 427 of the object 409 is outside of all of the retrieved ablation distances, the respective location 427 on the object 409 is assigned to the non-ablated object region.

Also this concept with the ablation distances and angles for parameterizing two-dimensional model ablation regions can be used with a first type of two-dimensional model ablation regions defining model ablation regions considering the influence of at least one model energy influencing element on the model ablation regions and a second type of model ablation regions not considering the influence of the at least one model energy influencing element on the model ablation regions. These different types of parameterized two-dimensional model ablation regions can then be used to determine an ablated object region of the object of interest, a first non-ablated object region of the object of interest, and a second non-ablated region of the object of interest.

Referring again to FIG. 1, a model ablation region determining apparatus 38 for determining model ablation regions is provided. The model ablation region determining apparatus 38 is adapted to determine the model ablation regions depending on a spatial relationship between a model ablation element and at least one model energy influencing element, wherein a model ablation region defines a region which will be ablated given the respective spatial relationship between the model ablation element and the at least one model energy influencing element. The model ablation region determining apparatus 38 is further adapted to store the determined model ablation regions in the model ablation region storing unit 4. The model ablation region determining apparatus 38 is adapted to determine the model ablation regions as described above in more detail.

It should be noted that the model ablation region determining apparatus 38 does not have to be a part of the ablated object region determining apparatus 1. The ablated object region determining apparatus 1 just needs the model ablation region storing unit 4 in which the already determined model ablation regions are stored. However, in another embodiment the model ablation region determining apparatus 38 can also be a part of the ablated object region determining apparatus 1.

The model ablation region determining apparatus 38 is adapted to determine a model ablation region by determining an ablation region using a model of partial differential equations, wherein only one model energy influencing element is present and has a cylindrical shape with circular or polygonal cross-section and is located in the vicinity of the model ablation element. Distances from the ablation element to the boundary of determined ablation region, in particular, distances from the center of the ablation element or from a location on an outer surface of the ablation element to the boundary of the determined ablation region, are determined, wherein this determination is performed in various directions and generally depends on the direction. These determinations are performed for different spatial relationships between the model ablation element and the model energy influencing element, in particular, for different locations on an outer surface of the model ablation element and different locations on an outer surface of the model energy influencing element, and the resulting distances and directions or angles are stored in the model ablation region storing unit 4 for storing the model ablation regions.

The partial differential equations used by the model ablation region determining apparatus 38 can be the equations described in the above mentioned articles.

Figure 11:
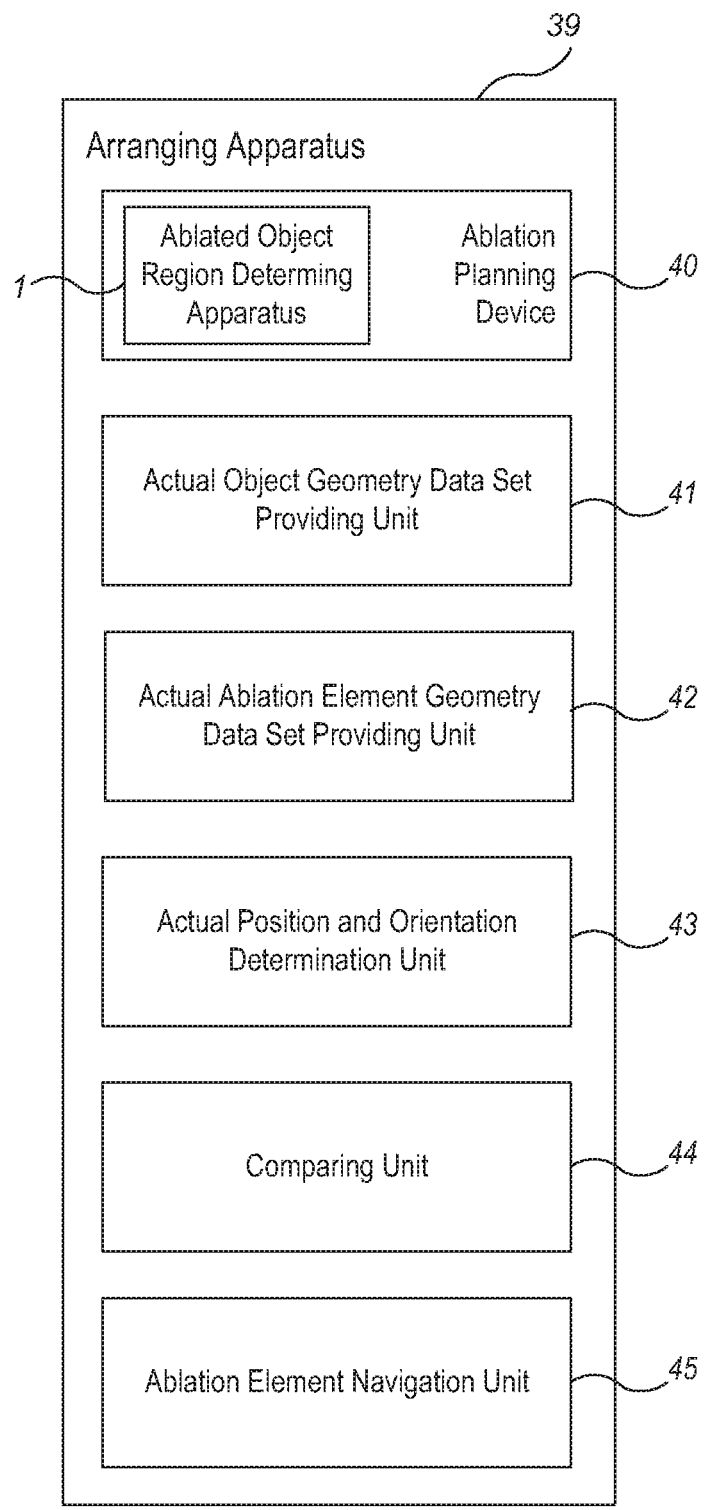
FIG. 11 shows schematically and exemplarily an embodiment of an arranging apparatus for arranging an ablation element within an object of interest.

FIG. 11 shows schematically and exemplarily an arranging apparatus 39 for arranging an ablation element within an object of interest. The arranging apparatus 39 comprises an ablation planning device 40, which includes the ablated object region determining apparatus 1, for planning a position and orientation of the ablation element such that a desired ablated object region is determined. The arranging apparatus further comprises an actual object geometry data set providing unit 41 for providing an actual object geometry data set showing the object of interest and an actual ablation element geometry data set providing unit 42 for providing an actual ablation element geometry data set showing the ablation element. The arranging apparatus 39 further comprises an actual position and orientation determination unit 43 for determining the actual position and orientation of the ablation element within the provided actual ablation element geometry data set and/or for determining the actual position of the object within the provided actual element geometry data set. The arranging apparatus 39 further comprises a comparing unit 44 for comparing the determined actual position and orientation of the ablation element with the planned position and orientation of the ablation element and an ablation element navigation unit 45 for navigating the ablation element to the planned position in the planned orientation. The ablation element navigation unit 45 is adapted to indicate the distance and the direction from the actual position in the actual orientation to the planned position in the planned orientation, if a deviation of the actual orientation from the planned orientation is larger than an orientation threshold and/or if a deviation of the actual position from the planned position is larger than a position threshold.

Figure 12:
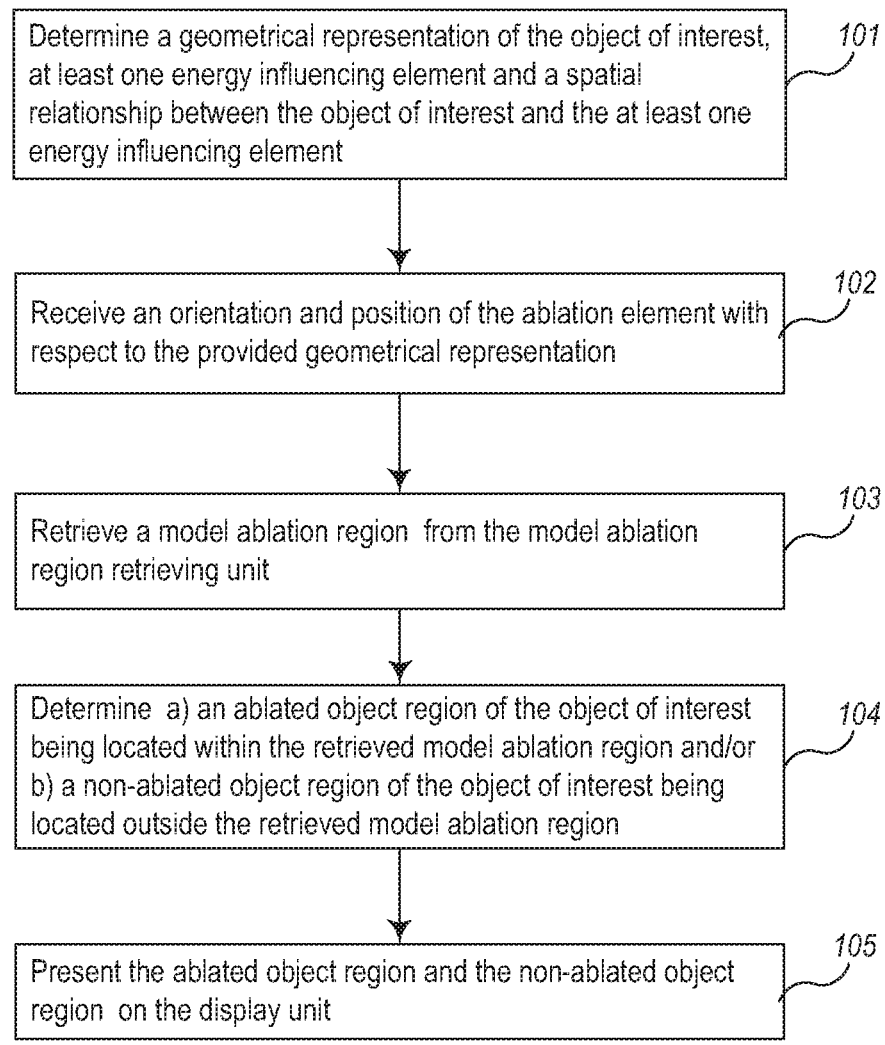
FIG. 12 shows a flowchart exemplarily illustrating an ablated object region determining method for determining an ablated object region for ablating an object of interest.

In the following an example embodiment of an ablated object region determining method will exemplarily be described with reference to a flowchart phone in FIG. 12.

In step 101, a geometrical representation of the object of interest, of at least one energy influencing element and of a spatial relationship between the object of interest and the at least one energy influencing element is provided by the geometrical representation providing unit 2. Then, in step 102 an orientation and position of the ablation element with respect to the provided geometrical representation can be set by using the ablation element setting unit 3. It should be noted, that not a real ablation element is oriented and positioned with respect to the provided geometrical representation, but a graphical representation of a real ablation element is oriented and positioned with respect to the provided geometrical representation by using the input unit 14 and the graphical user interface 15.

In step 103, a model ablation region is retrieved from the model ablation region retrieving unit 5. The retrieved model ablation region corresponds to the spatial relationship between the ablation element in the set orientation and in the set position and the at least one energy influencing element represented by the provided geometrical representation. The model ablation region is retrieved from the model ablation region storing unit 4 in which model ablation regions are stored depending on a spatial relationship between a model ablation element and at least one model energy influencing element.

In step 104, the ablated object region determining unit 6 determines at least one of a) an ablated object region of the object of interest being located within the retrieved model ablation region and b) a non-ablated object region of the object of interest being located outside the retrieved model ablation region. The ablated object region and the non-ablated object region are visualized differently on the display unit 7 in step 105.

By using the above described ablated object region determining apparatus and ablated object region determining method a user like a physician can set different orientations and positions of the ablation element, i.e. of the graphical representation of the ablation element, with respect to the provided geometrical representation and determine which part of the object of interest will be ablated and which part of the object of interest will not be ablated considering the respective set orientation and position of the ablation element. Thus, the outcome of an actual ablation procedure to be performed can be predicted before the actual ablation procedure is performed. This prediction can be provided very fast, because the model ablation regions have already been determined and just have to be retrieved from the model ablation region storing unit 4.

Figure 13:
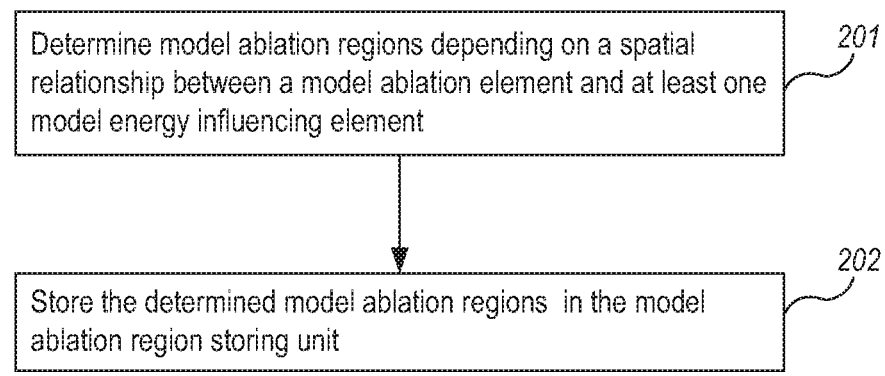
FIG. 13 shows a flowchart exemplarily illustrating a model ablation region determining method for determining model ablation regions.

In the following an example embodiment of a model ablation region determining method will exemplarily be described with reference to a flowchart shown in FIG. 13.

In step 201, ablation regions are determined depending on a spatial relationship between a model ablation element and at least one model energy influencing element, wherein a model ablation region defines a region which will be ablated given the respective spatial relationship between the model ablation element and the at least one model energy influencing element. For a more detailed description of the determination of the model ablation regions reference is made to the above given explanations. In step 202, the determined model ablation regions are stored in the model ablation region storing unit 4.

Figure 14:
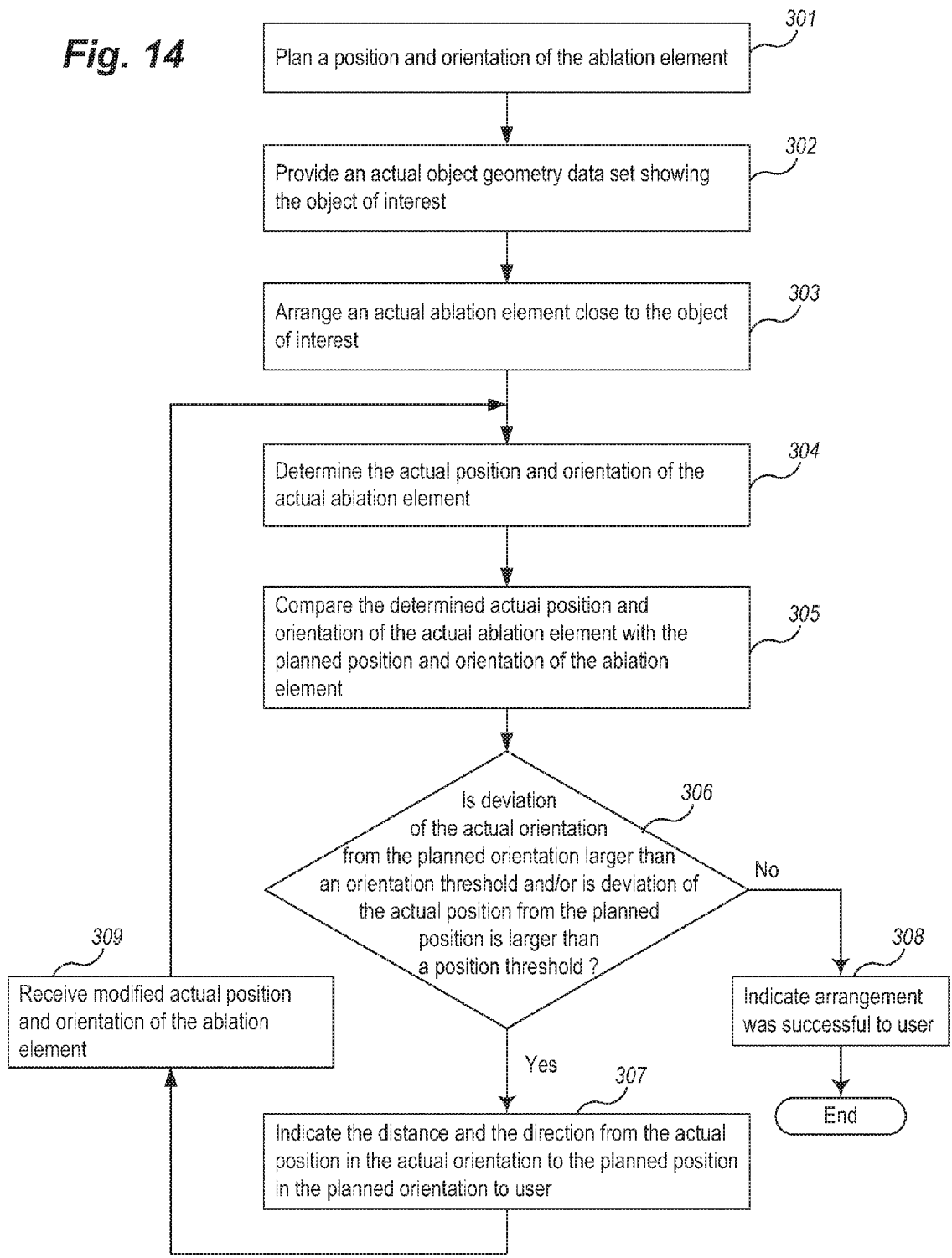
FIG. 14 shows a flowchart exemplarily illustrating an arranging method for arranging an ablation element within an object of interest.

In the following an embodiment of an arranging method will exemplarily be described with reference to a flowchart shown in FIG. 14.

In step 301, a position and orientation of the ablation element is planned depending on an ablated object region of the object of interest determined by the above described ablated object region determining method. For example, the position and orientation of the ablation element can be planned such that the determined ablated object region is maximized.

In step 302, an actual object geometry data set showing the object of interest is provided. The actual object geometry data set is, for example, a medical image data set. In step 303 a user like a radiologist arranges an actual ablation element, i.e. a real ablation element, within or close to the object of interest. For example, a user like a radiologist inserts an ablation element into a patient such that the ablation element is located within or close to the object of interest. In step 304, the actual position and orientation of the actual ablation element within the provided actual object geometry data set are determined. In step 305, the determined actual position and orientation of the actual ablation element is compared with the planned position and orientation of the ablation element, and in step 306 it is determined if a deviation of the actual orientation from the planned orientation is larger than an orientation threshold and/or if a deviation of the actual position from the planned position is larger than a position threshold. If this is the case, in step 307 the distance and the direction from the actual position in the actual orientation to the planned position in the planned orientation is indicated to the user, for example, shown on the display unit 7. Then, in step 309, the user can modify the actual position and orientation of the ablation element as indicated in step 307, and the arranging method continues with step 304. If in step 306 it is determined that the deviation of the actual orientation from the planned orientation is not larger than the orientation threshold and that the deviation of the actual position from the planned position is not larger than the position threshold, in step 308 it is indicated to a user that the arrangement was successful. This indication can also be provided on the display unit 7 and/or an acoustical signal can be provided indicating a successful arranging procedure.

After it has been indicated to the user that the arrangement was successful in step 308, optionally the user can modify the actual position and orientation of the ablation element again and the arranging method continues with step 304, and/or the user can place a further ablation element, wherein the arranging method continues with step 302.

In step 304 the actual position and orientation of the actual ablation element within the provided actual object geometry data set is determined by an electromagnetic tracking and/or an optical tracking of the actual ablation element. Also the actual position and orientation of the actual ablation element within the actual object geometry data set can be obtained through image acquisition like CT fluoroscopy and subsequent segmentation of the actual ablation element from the acquired image if the actual ablation element has been inserted into a patient.

It should be noted that the ablation element navigation unit does not have to be adapted to navigate the ablation element by itself. The ablation element navigation unit is adapted to indicate distances and directions between an actual position in an actual orientation and a planned position in a planned orientation of the ablation element, in order to provide a user with information which allows the user to correct the arrangement.

Other variations to the disclosed embodiments can be understood and incorporated by those skilled in the art in practicing embodiments, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Providing procedures like providing geometrical representations, storing procedures like storing model ablation regions, retrieving procedures like retrieving model ablation regions and determining procedures like determining ablated object regions and/or non-ablated object regions performed by one or several units or devices can be performed by any other number of units or devices. For example, steps 101 to 105 can be performed by a single unit like a computer or by any other number of different units. The above mentioned procedures like providing procedures, setting procedures, storing procedures, retrieving procedures, determination procedures, arranging procedures etc. and/or the control of the ablated object region determining apparatus in accordance with the ablated object region determining method and/or the control of the model ablation region determining apparatus in accordance with the model ablation region determining method and/or the control of the arranging apparatus in accordance with the arranging method can be implemented as program code or other instruction means of a computer program and/or as dedicated hardware using a general purpose or special purpose computer system appropriately programmed to achieve such methods.

A computer program may be stored/distributed on a suitable medium, such as an optical storage medium or a solid-state medium, or other computer-readable or storage medium, supplied together with or as part of other hardware, but may also be stored and transmitted or distributed in other forms, such as via the Internet or other wired or wireless telecommunication systems.

Any reference signs in the claims should not be construed as limiting the scope.

The present disclosure relates to an ablated object region determining apparatus for determining an ablated object region for ablating an object of interest. A user can set an orientation and position of an ablation element with respect to a geometrical representation of the object of interest, at least one energy influencing element and a spatial relationship between the object of interest and the at least one energy influencing element. A model ablation region retrieving unit retrieves a model ablation region depending on the respective set orientation and position of the ablation element from a model ablation region storing unit. An ablated object region determining unit determines at least one of a) an ablated object region of the object of interest being located within the retrieved model ablation region and b) a non-ablated object region of the object of interest being located outside the retrieved model ablation region.

The invention claimed is:

1. A model ablation region determining apparatus for predetermining model ablation regions decoupled from the determination of a desired at least one ablated object region of an object of interest to allow an ablation planning apparatus to determine the desired at least one ablated object region within a few seconds, comprising:
   a memory;
   a computer processor; and
   model ablation region program code, stored in the memory, and configured when executed on the computer processor to:
      determine the model ablation regions depending on determinations of energy distribution and a spatial relationship between a model ablation element and at least one model energy influencing element by solving linear or non-linear equations indicative of material properties of the object of interest and of the object of interest environment, wherein an model ablation region defines a region in which the determined energy distribution exceeds a threshold, which would be ablated when used in an ablation procedure given the respective spatial relationship between the model ablation element and the at least one model energy influencing element; and
      store the determined model ablation regions in a model ablation region storing unit such that the ablation planning apparatus can retrieve a stored model ablation region to determine the desired ablated object region within a few seconds.

2. A model ablation region determining method for predetermining model ablation regions decoupled from the determination of a desired at least one ablated object region of an object of interest to allow an ablation planning apparatus to determine the desired at least one ablated object region within a few seconds, comprising:
   determining the model ablation regions depending on determinations of energy distribution and a spatial relationship between a model ablation element and at least one model energy influencing element by solving linear or non-linear equations indicative of material properties of the object of interest and of the object of interest environment, wherein a model ablation region defines a region in which the determined energy distribution exceeds a threshold, which would be ablated when used in an ablation procedure given the respective spatial relationship between the model ablation element and the at least one model energy influencing element; and storing the determined model ablation regions in a model ablation region storing unit such that the ablation planning apparatus can retrieve a stored model ablation region to determine the desired ablated object region within a few seconds.

3. A computer-readable storage medium containing an ablated object region determining computer program for determining an ablated object region for ablating an object, the computer program comprising program code that causes a model ablation region determining apparatus to determine at least one model ablated object region when the computer program is executed on a computer controlling the model ablation region determining apparatus by performing steps of:

providing a geometrical representation of the object of interest, of at least one energy influencing element and of a spatial relationship between the object of interest and the at least one energy influencing element;

setting an orientation and position of the ablation element with respect to the provided geometrical representation;

retrieving a predetermined model ablation region, that corresponds to determined energy distribution and the spatial relationship between the ablation element in the set orientation and in the set position and the at least one energy influencing element represented by the provided geometrical representation, from a model ablation region storing unit in which model ablation regions are stored depending on a spatial relationship between a model ablation element and at least one model energy influencing element, wherein the predetermined model ablation region defines a region that will be ablated when used in an ablation procedure given the respective spatial relationship between the model ablation element and the at least one model energy influencing element; and determining a) an ablated object region of the object of interest being located within the retrieved model ablation region and/or b) a non-ablated object region of the object of interest, being located outside the retrieved model ablation region, within a few seconds.

4. A computer-readable storage medium containing a model ablation region determining computer program for predetermining model ablation regions decoupled from the determination of a desired at least one ablated object region of an object of interest to allow an ablation planning apparatus to determine the desired at least one ablated object region within a few seconds, the computer program comprising program code that causes a model ablation region determining apparatus to determine model ablated object regions when the computer program is executed on a computer controlling the model ablation region determining apparatus, by performing the steps of:

determining the model ablation regions depending on determinations of energy distribution and a spatial relationship between a model ablation element and at least one model energy influencing element by solving linear or non-linear equations indicative of material properties of the object of interest and of the object of interest environment, wherein a model ablation region defines a region in which the determined energy distribution exceeds a threshold, which would be ablated when used in an ablation procedure given the respective spatial relationship between the model ablation element and the at least one model energy influencing element; and storing the determined model ablation regions in a model ablation region storing unit such that the ablation planning apparatus can retrieve a stored model ablation region to determine the desired ablated object region within a few seconds.

* * * * *